(12) United States Patent
Petersen et al.

(10) Patent No.: US 7,678,146 B2
(45) Date of Patent: Mar. 16, 2010

(54) POLYACRYLAMIDE HYDROGEL AND ITS USE AS AN ENDOPROSTHESIS

(75) Inventors: Jens Petersen, Birkerød (DK); Richard Schmidt, Vedbæk (DK); Robert Lessèl, Brøndby (DK); Jens-Erik Sørensen, Hellerup (DK)

(73) Assignee: Contura A/S, Montreux (CH)

( * ) Notice: Subject to any disclaimer, the term of this patent is extended or adjusted under 35 U.S.C. 154(b) by 0 days.

(21) Appl. No.: 09/938,670

(22) Filed: Aug. 27, 2001

(65) Prior Publication Data

US 2002/0064512 A1     May 30, 2002

Related U.S. Application Data

(60) Provisional application No. 60/228,081, filed on Aug. 25, 2000.

(51) Int. Cl.
*A61F 2/02* (2006.01)
*A61K 9/14* (2006.01)

(52) U.S. Cl. .................. 623/11.11; 424/486; 424/78.31

(58) Field of Classification Search ................ 623/6.59, 623/8, 11.11, 23.58, 23.72; 424/422–424, 424/484–489, 78.31, 78.35, 78.37, 78.38, 424/486, 426, 793.7; 523/113–115; 514/724, 514/725; 435/177–179
See application file for complete search history.

(56) References Cited

U.S. PATENT DOCUMENTS

| | | | |
|---|---|---|---|
| 3,661,659 A * | 5/1972 | Breza | 149/19.91 |
| 3,713,981 A * | 1/1973 | Broadbent et al. | 435/223 |
| 3,867,329 A | 2/1975 | Halpern et al. | |
| 3,948,862 A | 4/1976 | Iwasyk | |
| 4,074,039 A * | 2/1978 | Lim et al. | 526/306 |
| 4,344,193 A | 8/1982 | Kenny | |
| 4,371,519 A * | 2/1983 | Hettinger, Jr. | 424/78.35 |
| 4,502,161 A | 3/1985 | Wall | |
| 4,535,131 A | 8/1985 | Handa et al. | |
| 4,540,427 A * | 9/1985 | Helbling | 71/27 |
| 4,540,568 A | 9/1985 | Trager et al. | |
| 4,540,569 A | 9/1985 | Ohnishi et al. | |
| 4,571,749 A | 2/1986 | Fischell | |
| 4,579,578 A * | 4/1986 | Cooke | 71/11 |
| 4,657,656 A | 4/1987 | Ogawa | |
| 4,713,434 A | 12/1987 | Sutterlin et al. | |
| 4,746,551 A | 5/1988 | Allen et al. | |
| 4,857,041 A | 8/1989 | Annis et al. | |
| 4,919,667 A | 4/1990 | Richmond | |
| 4,969,474 A | 11/1990 | Schwarz | |
| 4,997,537 A * | 3/1991 | Karger et al. | 204/453 |
| 5,135,480 A | 8/1992 | Bannon et al. | |
| 5,171,322 A | 12/1992 | Kenny | |
| 5,244,799 A | 9/1993 | Anderson | |
| 5,306,404 A | 4/1994 | Notsu et al. | |
| 5,344,451 A | 9/1994 | Dayton | |
| 5,344,459 A | 9/1994 | Swartz | |
| 5,482,719 A | 1/1996 | Guillet et al. | |
| 5,516,531 A | 5/1996 | Atala et al. | |
| 5,589,104 A | 12/1996 | Bambeck | |
| 5,652,274 A * | 7/1997 | Martin | 514/724 |
| 5,658,329 A * | 8/1997 | Purkait | 623/23.72 |
| 5,667,778 A | 9/1997 | Atala | |
| 5,700,289 A * | 12/1997 | Breitbart et al. | 424/423 |
| 5,709,854 A | 1/1998 | Griffith-Cima et al. | |
| 5,798,096 A | 8/1998 | Pavlyk | |
| 5,813,411 A | 9/1998 | Van Bladel et al. | |
| 5,854,382 A | 12/1998 | Loomis | |
| 5,902,832 A | 5/1999 | Van Bladel | |
| 5,941,909 A | 8/1999 | Purkait | |
| 6,005,020 A | 12/1999 | Loomis | |
| 6,060,053 A | 5/2000 | Atala | |
| 6,129,761 A | 10/2000 | Hubbell | |
| 6,252,016 B1 | 6/2001 | Wu et al. | |
| 6,277,948 B1 | 8/2001 | Zahr | |
| 6,335,028 B1 | 1/2002 | Vogel et al. | |
| 6,486,213 B1 | 11/2002 | Chen et al. | |
| 6,544,503 B1 | 4/2003 | Vanderhoff et al. | |
| 6,592,859 B1 | 7/2003 | Bley | |
| 6,660,301 B1 * | 12/2003 | Vogel et al. | 424/489 |
| RE38,913 E | 12/2005 | Pavlyk | |
| 2002/0187172 A1 | 12/2002 | Reb et al. | |
| 2003/0171509 A1 | 9/2003 | Balestrieri et al. | |
| 2005/0175704 A1 | 8/2005 | Petersen | |

FOREIGN PATENT DOCUMENTS

CN    1228447    9/1999

(Continued)

OTHER PUBLICATIONS

U.S. Appl. No. 09/938,667, filed Aug. 27, 2001 Jens Petersen.

(Continued)

*Primary Examiner*—David J. Isabella
(74) *Attorney, Agent, or Firm*—Hunton & Williams LLP (57) ABSTRACT

A biocompatible hydrogel comprises a specified content of polyacrylamide and pyrogen-free water. Also disclosed is a method of making the hydrogel and an injectable or implantable endoprosthesis. The hydrogel may also be used to treat a cosmetic or functional defect. Hydrogels specified according to their polyacrylamide content may be used for medical indications, such as an implantable or injectable endoprostheses for mammoplastic reconstruction, implantable or injectable endoprostheses for treating (reflux) oesophagitis, and for body contouring of various body parts.

19 Claims, No Drawings

FOREIGN PATENT DOCUMENTS

| | | |
|---|---|---|
| EP | 0153672 | 9/1985 |
| EP | 0153672 B1 | 9/1985 |
| EP | 0 248 544 | 12/1987 |
| EP | 0496067 A2 | 7/1992 |
| EP | 055119 A1 | 8/1993 |
| EP | 0727232 A2 | 8/1996 |
| EP | 0 730 847 | 9/1996 |
| EP | 0727232 A3 | 11/1996 |
| EP | 0742022 A1 | 11/1996 |
| EP | 0 774 981 | 5/1997 |
| EP | 0 826 381 | 3/1998 |
| EP | 0 830 416 | 3/1998 |
| EP | 0 895 785 | 2/1999 |
| EP | 1 059 943 | 12/2000 |
| EP | 1 274 472 | 1/2003 |
| GB | 1317408 | 5/1973 |
| GB | 1320233 | 6/1973 |
| GB | 2114578 | 6/1980 |
| GB | 2114578 | 5/1981 |
| RU | SU 1697756 A1 | 6/1988 |
| RU | 2034465 | 5/1995 |
| RU | 2148957 | 2/1998 |
| RU | 2127129 | 3/1999 |
| RU | 2148957 | 5/2000 |
| SU | 1608193 | 11/1990 |
| SU | 1687291 | 10/1991 |
| SU | 1831709 | 7/1993 |
| WO | WO 81/01290 | 5/1981 |
| WO | WO89/07455 | 8/1989 |
| WO | 93/19702 | 10/1993 |
| WO | 96/39464 | 12/1995 |
| WO | 96/04026 | 2/1996 |
| WO | 96/04943 | 2/1996 |
| WO | 96/25129 | 8/1996 |
| WO | 98/25575 | 6/1998 |
| WO | WO99/10021 | 3/1999 |
| WO | 99/15211 | 4/1999 |
| WO | 99/44643 | 9/1999 |
| WO | 00/31148 | 6/2000 |
| WO | 00/59411 | 10/2000 |
| WO | WO 00/78356 | 12/2000 |
| WO | 01/32129 | 5/2001 |
| WO | 01/38402 | 5/2001 |
| WO | 01/42312 A1 | 6/2001 |
| WO | 01/47431 | 7/2001 |
| WO | 01/47433 | 7/2001 |
| WO | 01/50833 | 7/2001 |
| WO | WO 01/49336 A1 | 7/2001 |
| WO | 01/70289 | 9/2001 |

OTHER PUBLICATIONS

U.S. Appl. No. 09/938,668, filed Aug. 27, 2001 Jens Petersen.
U.S. Appl. No. 09/938,669, filed Aug. 27, 2001 Jens Petersen.
Gebauer et al., Gonarthritis due to Salmonella enteritidis in a patient with systemic lupus erythematosus, Klinische Padiatrie, (Sep.-Oct. 2002) 214 (5), 319-323, ABSTRACT.
Jarosova et al., Analysis of clinical and laboratory data in a group of patients with juvenile idiopathic arthritis (JIA) in the framework of the national register, Ceska Revmatologie, (2002) 10/2 (65/70), ABSTRACT.
International Search Report dated Jan. 31, 2002, for Application PCT/DK01/00565, filed Aug. 25, 2001.
U.S. Appl. No. 10/227,265, Aug. 26, 2002 Richard Schmidt, et al.
RU Lic. Reg. No. 94, May 20, 1994, Russion Fed, Irkutsk Region, License to Medical Insurance of Citizens in the RSFSR Act, Abstract.
N.A. Peppas, 1986, *Hydrogels in Medicine and Pharmacy*, CRC Press, vol. I, pp. 2-6; 96-97.
U.S. Appl. No. 11/469,213, Aug. 31, 2006 Petersen.
Stevens, Malcolm P., Definitions, "Polymer Chemistry: An Introduction", Third Edition, Oxford University Press, Inc., Sect. 1.2, pp. 6-10, 1999.
Lewis, Richard J., Sr., Olifin (alkene), "Hawley's Condensed Chemical Dictionary", Thirteenth Edition, John Wiley & Sons, Inc., pp. 819, 1997.
O'neil, Maryadele J., et al. (Eds.), Acrylamide, "The Merck Index: An Encyclopedia of Chemicals, Drugs, and Biologicals", Thirteenth Edition, Merck Research Laboratories, Merck & Co., Inc., Listing No. 131, pp. 128, 2001.
Ministry of Public Health of Ukraine, Kiev Research Institute of Hematology and Blood Transfusion, Report dated Feb. 29, 1993.
Interfall's Biocompatible Hydrogel, Doctor's Information (Feb. 22, 2006) (citing U.S. Appl. No. 5,798,096) *at* http://www.bpg.bg/interfall/EB005140106biocompatible$_{13}$gel1.htm.
J.E. Gomez and G.B. Thurston, Comparisons of the oscillatory shear viscoelasticity and composition of pathological synovial fluids, Biorheology 30, 409-427 (1993).
International Search Report dated Jan. 31, 2002, for Application PCT/DK01/00565, Filed Aug. 25, 2001.

\* cited by examiner

POLYACRYLAMIDE HYDROGEL AND ITS USE AS AN ENDOPROSTHESIS

REFERENCE TO PRIOR APPLICATION

This application claims priority under 35 U.S.C. § 119(e) from provisional application Ser. No. 60/228,081, filed Aug. 25, 2000, which is incorporated herein by reference to the extent it is consistent with this application.

FIELD OF INVENTION

The present invention relates to a novel polyacrylamide hydrogel cross-linked polyacrylamide. The hydrogel is obtainable by combining the acrylamide and methylene bis-acrylamide in a specific ratio so as to confer physical properties to the hydrogel. The present invention further relates to the use of the hydrogel for the preparation of an endoprosthesis for cosmetic surgery, reconstructive surgery, and therapy.

BACKGROUND OF THE INVENTION

Natural and synthetic polymers such as collagen, soya, glycerol, silicone, polyvinylpyrolidone and hyaluronic acid have been utilised as endoprostheses. Materials used for endoprostheses generally try to imitate the natural soft tissue and are intended to be safe to the health of the patient.

Polyacrylamide gels have also been disclosed. U.S. Pat. No. 5,798,096 relates to a biocompatible hydrogel containing 3.5 to 6.0% cross-linked polyacrylamide. However, U.S. Pat. No. 5,798,096 teaches that concentrations below 3.5% make the hydrogel unstable.

GB 2114578 relates to a polyacrylamide gel for medical and biological purposes containing 3 to 28% polyacrylamide with the remainder of the mass of the gel comprised of a physiological solution.

U.S. Pat. No. 5,658,329 relates to an implantable endoprosthesis comprising a shell filled with a polyacrylamide gel comprising 2 to 20% polyacrylamide by weight and a viscosity range of 15 to 75 Pas.

Formacryl® polyacrylamide is a soft-tissue endoprosthesis consisting of 5% reticulated polyacrylamide polymer and 95% apyrogenic water commercialised as an injectable device for medical and dental use to correct congenital or acquired deficits such as wrinkles, lines and scars. It is to be implanted with a syringue in the hypodermis.

SUMMARY OF THE INVENTION

The present invention relates to a biocompatible hydrogel comprising i) less than 3.5% (wt/wt) polyacrylamide cross-linked with methylene bis-acrylamide and ii) pyrogen-free water. Specifically, it relates to a hydrogel comprising less than 3.5% by weight polyacrylamide obtainable by combining acrylamide and methylene bis-acrylamide, radical initiation, and washing with pyrogen-free water, said combining being in a molar ratio of 150:1 to 1000:1.

An object of the invention is a hydrogel for use as an injectable or implantable endoprosthesis comprising i) less than 3.5% (wt/wt) polyacrylamide cross-linked with methylene bis-acrylamide and ii) pyrogen-free water or saline solution.

The present invention further relates to a method for the preparation of a hydrogel comprising the steps of combining acrylamide and methylene bis-acrylamide, radical initiation, and washing with pyrogen-free water so as to give less than 3.5% by weight polyacrylamide.

A further object of the invention is an injectable or implantable endoprosthesis comprising i) less than 3.5% by weight polyacrylamide cross-linked with methylene bis-acrylamide and ii) pyrogen-free water or saline solution. The invention further relates to the use of a hydrogel comprising i) less than 3.5% by weight polyacrylamide cross-linked with methylene bis-acrylamide and ii) pyrogen-free water or saline solution for the preparation of an endoprosthesis for cosmetic surgery, reconstructive surgery and therapy. A method for the preparation of an injectable or implantable endoprosthesis comprising the steps of mixing acrylamide and methylene bis-acrylamide in a ratio so as to give less than 3.5% by weight polyacrylamide, radical initiation, and washing with pyrogen-free water or saline solution is disclosed herein.

Moreover, the invention relates to a method of treatment of a cosmetic or functional defect with an injectable or implantable biocompatible endoprosthesis comprising: a) preparation of a polyacrylamide hydrogel, said polyacrylamide hydrogel comprising less than 3.5% by weight and said polyacrylamide being cross-linked using methylene bis-acrylamide, b) injection or implantation a sufficient amount of said hydrogel into a region of the body affected by a cosmetic or functional defect.

Hydrogels with higher polyacrylamide content are also embodied in the present invention particularly in relation to certain medical indications. A further object of the invention relates to the use of a hydrogel comprising i) more than 9.5% polyacrylamide by weight, based on the total weight of the hydrogel, and ii) pyrogen-free water or saline solution for the preparation of an implantable endoprosthesis for mammoplastic reconstruction.

A still further object of the invention relates to use of a hydrogel comprising more than 9.5% polyacrylamide by weight, based on the total weight of the hydrogel, for the preparation of an implantable endoprosthesis for body contouring.

The treatment of reflux oesophagitis is addressed in the present invention. The use of a hydrogel comprising more than 6% polyacrylamide by weight, based on the total weight of the hydrogel, for the preparation of an implantable endoprosthesis for treating (reflux) oesophagitis is a further object of the invention as is a method for treating (reflux) oesophagitis comprising implanting or injecting a polyacrylamide hydrogel endoprosthesis wherein the hydrogel comprises more than 6% polyacrylamide by weight, based on the total weight of the hydrogel.

Mammoplasty is also addressed herein. The present invention further relates to a method of cosmetically altering a mammalian breast or of performing a partial or total mammoplastic reconstruction on a woman comprising implanting a polyacrylamide hydrogel wherein said hydrogel comprises more than 9.5% polyacrylamide by weight, based on the total weight of the hydrogel, and ii) pyrogen-free water or saline solution.

Cosmetic surgery on the body (excluding the face), referred to herein as body contouring is also addressed herein. The present invention is further directed to a method of cosmetically altering a mammalian body (body contouring) comprising implanting a polyacrylamide hydrogel endoprosthesis, wherein the hydrogel comprises more than 9.5% polyacrylamide by weight, based on the total weight of the hydrogel, and ii) pyrogen-free water or saline solution.

DETAILED DESCRIPTION OF THE INVENTION

Hydrogels and Their Preparation

The success of plastic or reconstructive surgery depends to a great extent on the physical properties of the materials utilised. They must most certainly be biocompatible, stable and non-toxic but they must also have physical properties that mimic the bodily tissue they are replacing, as in reconstructive surgery, or mimic the bodily tissue in the proximity of the endoprosthesis, as in cosmetic surgery.

Materials such as collagen are resorbed into the body over short periods of time. Silicone and Soya have encountered serious safety issues. There is currently a need for a safe, stable, biocompatible material that possesses the physical properties to mimic soft tissue.

The present inventors have surprisingly found that a polyacrylamide hydrogel comprising less than 3.5% polyacrylamide, based on the total weight of the hydrogel, is an effective endoprosthesis with advantageous physical properties. Contrary to U.S. Pat. No. 5,798,096, the polyacrylamide gel is stable. The hydrogel, as prepared by a process according to the present invention, is cross-linked with methylene bis-acrylamide to a degree such that the endoprosthesis prepared from said hydrogel possesses advantageous physical characteristics. The hydrogel according to the present invention is a new chemical entity as indicated by its novel and advantageous physical characteristics. These secondary characteristics are indicative that the degree of cross-linking in the hydrogel of the present invention differs greatly from polyacrylamide hydrogels prepared by disclosed processes. This degree of cross-linking is a critical contributor to its physical properties.

The present investigators have provided a bio-stable hydrogel obtainable by combining acrylamide and methylene bis-acrylamide in amounts so as to give about 0.5 to 25% by weight polyacrylamide, based on the total weight of the hydrogel; radical initiation; and washing with pyrogen-free water or saline solution. The bio-stable hydrogel typically has a molecular weight between $0.01 \times 10^6$ and $20 \times 10^6$. The polymer is resistant to biological degradation and is not permeable through biological membranes. The polyacrylamide hydrogel of the invention is fully biocompatible (according to ISO standard test ISO-10993). The polyacrylamide hydrogel does not have cytotoxic effect on human fibroblasts, is non-toxic, non-carcinogenic, non-allergenic, non-mutagenic, and resistant to enzymatic and microbiological degradation. Furthermore, the polymer is not water-soluble. A primary object of the invention is to provide a hydrogel comprising less than 3.5% polyacrylamide by weight, based on the total weight of the hydrogel, said hydrogel obtainable by combining acrylamide and methylene bis-acrylamide, radical initiation, and washing with pyrogen-free water or saline solution; said hydrogel being biocompatible, and said combining being in a molar ratio of 150:1 to 1000:1.

A primary object of the invention is to provide a hydrogel comprising less than 3.5% polyacrylamide by weight, based on the total weight of the hydrogel, said hydrogel obtainable by combining acrylamide and methylene bis-acrylamide, radical initiation, and washing with pyrogen-free water or saline solution; said hydrogel being biocompatible, and said combining being in a molar ratio of 150:1 to 1000:1.

Alternatively defined, the primary object of the invention relates to hydrogel comprising i) less than 3.5% polyacrylamide by weight, based on the total weight of the hydrogel, cross-linked with methylene bis-acrylamide and ii) at least 95% pyrogen-free water or saline solution.

A further aspect of the invention relates to a hydrogel for use as an injectable or implantable endoprosthesis said hydrogel comprising i) less than 3.5% polyacrylamide by weight, based on the total weight of the hydrogel, cross-linked with methylene bis-acrylamide and ii) at least 95% pyrogen-free water or saline solution.

In all embodiments wherein the hydrogel comprises less than 3.5% polyacrylamide by weight, based on the total weight of the hydrogel, the hydrogel typically further comprises at least 95% pyrogen-free water or saline solution.

The hydrogel comprises less than 3.5% polyacrylamide preferably comprising at least 0.5%, such as at least 1%, preferably at least 1.5% polyacrylamide, such as at least 1.6% polyacrylamide by weight, based on the total weight of the hydrogel.

The hydrogel of the invention are chemically stable and bio-stable but may be very fluid such that they may be characterised in that it has a complex viscosity not less than 2 Pas, such as not less than 3, 4 or 5 Pas. In a suitable embodiment, the hydrogel is characterised in that it has complex viscosity from about 2 to 90, such as 5 to 80 Pas, preferably from about 6 to 76, such as from about 6 to 60, 6 to 40, 6 to 20, such as 6 to 15 Pas.

The hydrogel of the invention has elastic properties in that the hydrogel may be characterised in that it has elasticity module of not less than 10 Pa, such as not less than 20, 25, 30, 31, 32, 33, 34 or 35 Pa, such as not less than 38 Pa. Typically, the hydrogel has an elasticity module from about 10 to 700 Pa, such as about 35 to 480 Pa.

These rheological features are due in part to the degree of cross-linking and to the degree of swelling of the hydrogel. The hydrogel may be characterised in that the cross-linked polyacrylamide is cross-linked to such a degree so as to have an efficient cross-linking density of about 0.2 to 0.5%, preferably about 0.25 to 0.4%.

The cross-lining density is in turn due in part to the molar ratio between the acrylamide and methylene-bis-acrylamide. Typically said ratio is in the range 175:1 to 800:1, such as from 225:1 to 600:1, preferably from 250:1 to 550:1, most preferably from 250:1 to 500:1. The absolute and relative amount of the redox agent (TEMED) and the initiator also influence the degree of cross-linking. As can be seen from Tables 1, 2, 3, 4, the present investigators have adjusted these parameters to influence the rheological properties of the hydrogel.

The biocompatible hydrogels of the invention may be suitably characterised, at least in part, by one or more of the following features: i) a cross-linking density of 0,2%.0.5; ii) an elasticity modulus (G') of 10 to 700 Pa; iii) a complex viscosity of 2 to 90 Pa s; iv) a dry matter content of less than 3.5% such as less than 3.4, such as less than 3.3, such as less than 3.2, such as less than 3.1, such as less than 3.0, such as less than 2.9, such as less than 2.8, such as less than 2.7, such as less than 2.6 Pa s; v) a refractive index between 1.33 and 1.34.

As stated, in all aspects of the invention wherein the hydrogel comprises less than 3.5% polyacrylamide by weight, based on the total weight of the hydrogel, the hydrogel further comprises at least 95% pyrogen-free water or saline solution. In all embodiments wherein the hydrogel further comprises saline solution, the hydrogel preferably comprises less than 3% polyacrylamide by weight, based on the total weight of the hydrogel.

The hydrogel of the invention is substantially free of materials which contribute to the solid weight content other than the acrylamide, methylene-bis-acrylamide and residual amounts (if any) of the initiators. The hydrogel is substantially free of any other polymeric content. The hydrogel further comprises at least 75% by weight pyrogen-free water or saline solution, preferably pyrogen-free water. In a suitable embodiment of the invention, the hydrogel comprises at least 80% by weight pyrogen-free water or saline solution, preferably at least 85%, more preferably at least 90%, even more preferably at least 95% by weight pyrogen-free water or saline solution.

The hydrogel comprises pyrogen-free water or saline solution. The combining of the reagents and the casting of the gel may therefore be done in pyrogen-free water or saline solution. The use of saline solution will clearly increase the total solid weight content of the hydrogel but does not significantly influence the polyacrylamide content during the polymerisation reaction.

A suitable saline solution has an osmolarity similar to that of interstitial fluid. Suitable saline solutions include but are not limited to the group selected from 0.25-1% aqueous sodium chloride, a Ringer-Lockart solution, an Earle solution, a Hanks solution, an Eagle medium, a 0.25-1% glucose solution, a potassium chloride solution, and a calcium chloride solution. In a preferred embodiment, the saline solution is an about 0.8-1% aqueous sodium chloride solution, such as a 0.8, 0.9 or 1% aqueous sodium chloride solution.

As stated, pyrogen-free water or saline solution is used for the washing process. The washing process serves, in part, to remove all but trace amounts of the monomers acrylamide and N,N'-methylene-bis-acrylamide. These monomers are toxic to the patient as well as detrimental to the stability of the hydrogel. The washing process is preferably such that the concentrations of the monomers acrylamide and N,N'-methylene-bis-acrylamide are below 50 ppm, more preferably below 40 ppm, such as below 30 ppm, most preferably below 20 ppm, typically below 10 ppm, typically below 5 ppm. In the method of the invention, the washing step comprises swelling the product for 50 to 250 hours, more typically for 70 to 200 hours.

The hydrogel was surprisingly found to be stable at very low solid weight content, contrary to the teachings of U.S. Pat. No. 5,798,096. Polyacrylamide hydrogels with a solid-weight content of 0.5% have been prepared by the present investigators. Preferred embodiments of the hydrogel of the invention comprise at least 0.5%, such as at least 1%, preferably at least 1.5% polyacrylamide, such as at least 1.6% polyacrylamide by weight, based on the total weight of the hydrogel.

The hydrogel is suitably a composite of cross-linked polyacrylamide chains and pyrogen-free water. Water contained in the hydrogel as part of a composite is loosely bound with the polymer chains. When present in a body, some of the water molecules move into the tissue by osmosis resulting in a smoothing out of the affected skin surface. In the embodiment wherein the hydrogel comprises saline solution, the iso-osmolarity of the saline solution with interstitial fluid minimises immune responses.

As mentioned, the physical properties of the hydrogel are influenced in part by the degree of cross-linking. The degree of cross-linking may be controlled in part by the molar ratio of cross-linking agent, methylene bis-acrylamide, to acrylamide.

Therefore, another object of the invention is a method for the preparation of a hydrogel comprising the steps of combining acrylamide and methylene bis-acrylamide, radical initiation, and washing with pyrogen-free water or saline solution so as to give less than 3.5% by weight polyacrylamide, based on the total weight of the polyacrylamide. The method is preferably such that the hydrogel comprises at least 0.5%, such as at least 1%, preferably at least 1.5% polyacrylamide, such as at least 1.6% polyacrylamide by weight, based on the total weight of the hydrogel.

In a especially preferred embodiment of the invention, the hydrogel is obtainable by combining acrylamide and methylene bis-acrylamide in amounts so as to give 1.6 to 3.5% by weight polyacrylamide and in a molar ratio of 150:1 to 1000:1, radical initiation, and washing with pyrogen-free water or saline solution.

The combining of acrylamide and methylene bis-acrylamide is preferably done in a molar ratio between acrylamide and methylene bis-acrylamide which is from 175:1 to 800:1, such as from 225:1 to 600:1, preferably from 250:1 to 550:1, most preferably from 250:1 to 500:1.

An illustrative preparation of the hydrogel according to the present invention is described in Example 1. The hydrogel having the desired physical properties has been obtained by combining acrylamide and methylene bis-acrylamide in a ratio of about 250:1, such as 252:1, 254:1, 256:1, 258:1 and 260:1, as well as by combining acrylamide and methylene bis-acrylamide in a ratio of about 500:1, such as 498:1, 496:1 494:1 492:1, or 490:1. The hydrogel according to the present invention preferably has a complex viscosity from about 2 to 90, such as 5 to 80 Pas, typically from about 6 to 76, such as from about 6 to 60, 6 to 40, 6 to 20, such as 6 to 15 Pas. In a suitable embodiment, the washing step comprises swelling the product of the radical initiation step until the complex viscosity is from about 6 to 100 Pas.

In a suitable embodiment of the invention, the hydrogel has a degree of cross-linking such that it has complex viscosity of not less than 2 Pas, such as not less than 3, 4 or 5 Pas, such as not less than 5.5 Pas, such as not less than 6 Pas, preferably not less than 6.2 Pas.

The elasticity module is an alternative physical characteristic of the hydrogel indicative, in part, of the degree of cross-linking of the hydrogel according to the present invention. Typically, the degree of cross-linking is such that the hydrogel has an elasticity module of not less than 10 Pa, such as not less than 25, 30, 31, 32, 33, 34 or 35 Pa, such as not less than 38 Pa. The gel may be characterised in that it has elasticity module from about 10 to 700 Pa, such as about 35 to 480 Pa.

As stated, in a most preferred embodiment, the hydrogel is obtainable by combining acrylamide and methylene bis-acrylamide in amounts so as to give 1.6 to 3.5% by weight polyacrylamide and in a molar ratio of 150:1 to 1000:1, radical initiation, and washing with pyrogen-free water or saline solution. The radical initiation step yields a hydrogel still comprising toxic reagents and not yet possessing the beneficial physical properties of the hydrogel of the present invention. The washing step comprises swelling the hydrogel produced from the radical initiation step until the complex viscosity is from about 2 to 90 Pas.

Alternatively measured, the washing step may comprise swelling the product of the radical initiation step until the elasticity module is elasticity module from about 10 to 700 Pa, such as from about 35 to 480 Pa.

By nature, a low degree of cross-linking typically results in a higher swelling rate consequently lowering the dry matter content (percentage acrylamide), as well as lowering the elasticity module and viscosity. Thus, in addition to the degree of cross-linking, the time the hydrogel is exposed to the washing step influences to a degree the physical properties of the gel.

Typically, the washing step comprises swelling the product for about 80 to 100 hours, such as 90-95 hours. This usually results in an increase in weight of the hydrogel of about 75 to 150%, usually around 100% increase.

Furthermore, the amounts of the free-radical initiator in the radical initiation step and the amount of co-initiator influences the chain length and thus the physical properties of the hydrogel. In a typical preparation of the hydrogel, N-,N-,N-,N-tetramethyl ethylene diamine (TMED) is used as the co-initiator and ammoniumpersulfate (APS) is used as the free-radical initiator (redox-system). Adequate amounts of initiator and co-initiator are required to obtain the hydrogel according to the invention. As an illustration, an insufficient amount of these reagents will result in shorter chain lengths and consequently influence the degree of cross-linking and hence the physical properties of the hydrogel. Other reaction conditions, such as temperature also influence chain length.

As stated, the degree of cross-linking influences the physical properties of the hydrogel. The degree of cross-linking of the hydrogel of the present invention may be indirectly measured, as described above, by the elasticity module and/or by the complex viscosity. An alternative measure of the degree of cross-linking of the hydrogel is its efficient cross-linking density. The hydrogel of the present invention preferably comprises 1.6 to 3.5% (wt/wt) polyacrylamide cross-linked with methylene bis-acrylamide and ii) pyrogen-free water or saline solution, preferably such that the degree of cross-linking as measured by its efficient cross-linking density is such that the efficient cross-linking density is about 0.2 to 0.5%, preferably about 0.25 to 0.4%.

In a suitable embodiment of the present invention, the hydrogel may comprise 1.6 to 3.25% (wt/wt) polyacrylamide, such as 1.8 to 3.1, 2.0 to 3.0, 2.0 to 2.9, preferably 2.0 to 2.8 (wt/wt) polyacrylamide.

Medical Use of Polyacrylamide Hydrogels

The hydrogels of the invention are intended for use as endoprosthetic devices. The endoprosthetic devices of the invention and methods of treatment described herein may use the hydrogel in any of the embodiments described supra.

The endoprosthetic device may be administered to the body of an individual by means of injection, such as through a syringe or catheter or by means of surgical implantation. In the embodiment wherein the hydrogel is for use as an implantable endoprosthesis, the hydrogel may optionally serve as filler material in an envelope, the whole of which is implanted into the body. Thus the hydrogel or the endoprosthesis may comprise a silicone-based envelope housing the hydrogel.

As stated, an object of the invention is a method of treatment of a cosmetic or functional defect with an injectable biocompatible endoprosthesis comprising:
a) preparation of a 1.6 to 3.5% by weight polyacrylamide hydrogel, said polyacrylamide cross-linked using methylene bis-acrylamide,
b) injection a sufficient amount of said hydrogel into a region of the body affected by a cosmetic or functional defect. The hydrogel injected into an affected area is obtainable by combining acrylamide and methylene bis-acrylalmide in amounts so as to give 1.6 to 3.5% by weight polyacrylamide and in a molar ratio of 150:1 to 1000:1, radical initiation, and washing with pyrogen-free water or saline solution. The ratio of acrylamide to methylene bis-acrylamide is preferably such that the complex viscosity is from about 2 to 90, such as 5 to 80 Pas, preferably from about 6 to 76 Pas or such that the elasticity module is from about 10 to 700 Pa, such as about 35 to 480 Pa. The washing step may be done to the extent such that the complex viscosity is from about 6 to 80 Pas or such that the elasticity module is from 10 to 700 Pa, such as about 35 to 480 Pa.

The endoprosthetic device may comprise any of embodiments of the hydrogels discussed herein and may be either implantable or injectable Thus an important aspect of the present invention is the use of a hydrogel comprising i) less than 3.5% by weight polyacrylamide cross-linked with methylene bis-acrylamide and ii) at least 95% pyrogen-free water or saline solution for the preparation of an endoprosthesis for cosmetic surgery, reconstructive surgery and therapy. In particularly interesting embodiments of invention, the endoprosthesis is injectable.

A further object of the invention is a hydrogel as described supra for use in the preparation of an endoprosthesis. Specifically, an object of the invention is the use of a hydrogel comprising i) 1.6 to 3.5% by weight polyacrylamide cross-linked using methylene bis-acrylamide and ii) pyrogen-free water or saline solution for the preparation of an endoprosthesis for cosmetic surgery, reconstructive surgery and therapy. The endoprosthesis according to the present invention may be implantable or injectable. The cosmetic and reconstructive surgery may be for facial correction such as for altering the form or size of lips, to treat wrinkles or facial asymmetries, or altering the shape of a nose as well as a variety of facial corrections known to the person skilled in the art. Furthermore, cosmetic and reconstructive surgery may be to correct defects caused by trauma or due to diseases such as, for instance, hemiphlegia.

A hydrogel as described supra may be used for the preparation of an endoprosthesis. Thus, a further object of the present invention is an injectable endoprosthesis comprising i) 1.6 to 3.5% by weight polyacrylamide cross-linked with methylene bis-acrylamide and ii) pyrogen-free water or saline solution. An injectable endoprosthesis according to the present invention preferably has a complex viscosity from about 2 to 90, such as 5 to 80 Pas, preferably from about 6 to 76, such as from about 6 to 60, 6 to 40, 6 to 20, such as 6 to 15 Pas.

Wherein the endoprosthesis is injected, the hydrogel is generally somewhat fluid in nature.

Many disorders are related to a loss of effective activity of the tissue at a functional interface between two organs. For instance, urinary incontinence is related to insufficient sphincter between the urinary bladder and the urethra. By injecting or implanting an endoprosthesis prepared from the hydrogel according to the present invention into the proximal submucosa of the urethra, thereby narrowing the urethra, the disorder may be significantly controlled. Similarly, reflux oesophagitis is related to insufficient resistance between the oesophagus and stomach. By injecting or implanting an endoprosthesis prepared from the hydrogel according to the present invention along the sphincter between the oesophagus and stomach, the contact between the contents of the stomach and the oesophagus may be reduced. Thus, in suitable embodiments, the hydrogel is used for the preparation of an endoprosthesis to treat urinary incontinence or reflux oesophagitis. The endoprosthesis may, in general, be used to treat disorders related to insufficient resistance at a functional interface between two organs or between segments of one organ.

The solid-weight content of weight percentage acrylamide, as measured after the washing step, as well as the degree of cross-linking is adapted according to the use of the endoprosthesis prepared from the hydrogel. In preferred embodiments, the endoprosthesis is preferably prepared from a hydrogel comprising 1.6 to 3.25% (wt/wt) polyacrylamide, such as 1.8 to 3.1, 2.0 to 3.0, 2.0 to 2.9, preferably 2.0 to 2.8 (wt/wt) polyacrylamide. Alternatively defined, the degree of cross-linking of the hydrogel for use as an endoprosthesis may preferably be such that the complex viscosity of the hydrogel is from about 2.0 to 15 Pas such as from about 5.5 to 15 Pas, such as from 6 to 12 Pas. Alternatively measured, for facial corrections the degree of cross-linking of the hydrogel is preferably such that the elasticity module is from about 10 to 100 Pa, such as about 35 to 75, particularly 35 to 60 Pa, such as 35 to 50 Pa.

The endoprosthesis may be to correct a defect which is the result of trauma such as tumours or physical injury as well as congenital defects.

In a suitable embodiment of the present invention, the hydrogel as described supra is used as a filling material to fill or partially fill a silicone-based reservoir or shell for the preparation of an implantable endoprosthesis. Thus, a further object of the present invention is an implantable endoprosthesis comprising i) a hydrogel comprising 1.6 to 3.5% (wt/wt) polyacrylamide cross-linked with methylene bis-acrylamide and pyrogen-free water or saline solution ii) a silicone-based shell adapted for containing said hydrogel. The hydrogel used to fill or partially fill the silicone-based shell may be a hydrogel obtainable by combining acrylamide and methylene bis-acryalmide in amounts so as to give 1.6 to 3.5% by weight polyacrylamide and in a molar ratio of 150:1 to 1000:1, radical initiation, and washing with pyrogen-free water or saline solution. In embodiments wherein the endoprosthesis is implantable, the preparation of said endoprosthesis from a hydrogel optionally further comprises the step of inserting said hydrogel into a silicone-based shell.

After the hydrogel has been placed into the silicone-based shell, it can preferably be sealed by chemical, mechanical or thermal means or by laser or light. Typically, the outer surface of the shell is chemically or physically modified such that it is biocompatible and have a friction coefficient so as to minimise movement or slippage from the position it was placed.

In an alternative embodiment of the invention, the endoprosthesis may comprise a medicament for use in therapy. In a further suitable embodiment, any of the endoprostheses of the invention may further comprise of cells, such as stem cells, for cellular engraftment.

According to the present invention, the endoprosthesis is for mammoplastic augmentation or reconstruction, treating reflux oesophagitis, body contouring and penis enlargement.

Mammoplasty

The use of the hydrogel comprising i) less than 3.5% by weight polyacrylamide and at least 95% pyrogen-free water or saline solution for the preparation of an endoprosthesis for mammoplastic reconstruction is a preferred embodiment of this aspect of the present invention. It is most preferably implantable and further comprises a silicone-based envelope housing the hydrogel.

In the embodiment wherein the hydrogel comprises less than 3.5% by weight polyacrylamide, the hydrogel preferably comprises at least 1% by weight polyacrylamide, based on the total weight of the hydrogel, preferably at least 1.5%, such as at least 1.6% by weight polyacrylamide, based on the total weight of the hydrogel.

The hydrogels used for mammoplasty which comprise less than 3.5% by weight polyacrylamide are preferably injectable. Said injectable endoprostheses according to the present invention preferably have a complex viscosity from about 2 to 90, such as 5 to 80 Pas, preferably from about 6 to 76, such as from about 6 to 60, 6 to 40, 6 to 20, such as 6 to 15 Pas.

A further object of the invention is based on the preparation by the present investigators of a hydrogel with a higher solid-weight content. The use of a hydrogel comprising i) more than 9.5% polyacrylamide by weight, based on the total weight of the hydrogel, and ii) pyrogen-free water or saline solution for the preparation of an endoprosthesis for mammoplastic augmentation or reconstruction is a further object of the invention. Stated otherwise, a further object of the invention is a method of cosmetically altering a mammalian breast or of performing a partial or total mammoplastic reconstruction on a woman comprising implanting a polyacrylamide hydrogel endoprosthesis; wherein said hydrogel comprises more than 9.5% polyacrylamide by weight, based on the total weight of the hydrogel, and ii) at least 75% pyrogen-free water or saline solution.

In the embodiment wherein the hydrogel for mammoplasty comprises more than 9.5% polyacrylamide by weight, based on the total weight of the hydrogel, the hydrogel typically comprises less than 25% by weight polyacrylamide, based on the total weight of the hydrogel, such as less than 20%.

Endoprosthetic device for mammoplasty wherein the hydrogel comprises more than 9.5% polyacrylamide by weight are typically implantable. In said embodiments, the endoprosthesis may further comprisee a silicone-based envelope.

In the rectification of a partial or complete mastectomy, the endoprosthesis may be injectable or implantable. Wherein the endoprosthesis is implanted, the endoprosthesis may comprise a hydrogel according to the present invention in itself. The size and shape of the gel may be fixed by preparing the gel in a mould or cast or by sculpting the gel to the desired shape and size. Alternatively, prior or while implanting the gel, it may be inserted into a silicone-based shell which serves in part to contain said hydrogel.

In embodiments wherein an implantable endoprosthesis comprising a silicone-based shell is preferred, the hydrogel may be somewhat fluid or of a fixed resting shape. In embodiments wherein the endoprosthesis further comprises a silicone-based shell and the hydrogel is of a fixed resting shape, the size and shape is adapted to the requirements of the patient and may be fixed by preparing the gel in a mould or cast or by sculpting the gel to the desired shape and size. The shell may also be adapted to the size and shape of the hydrogel which it will contain. In embodiments wherein the implantable endoprosthesis does not comprise a silicone-based shell but rather that the hydrogel itself is implanted, the hydrogel is generally of a fixed resting shape. As stated, the shape and size may be adapted to the requirements of the patient and may be fixed by preparing the gel in a mould or cast or by sculpting the gel to the desired shape and size.

Wherein the endoprosthesis is injected for rectification of a partial or complete mastectomy, the endoprosthesis is preferably prepared from a hydrogel comprising 2.0 to 3.0% polyacrylamide, such as 2.2 to 3.0% polyacrylamide and having a complex viscosity of about 10 to 90 Pas, such as 20 to 90, 30 to 90, or 40 to 80 Pas and an elasticity module of about 50 to 700 Pa such as 75 to 600, such as 100 to 500, preferably about 200 to 500 Pa. Typically, the hydrogel has a complex viscosity of at least 10 Pa.s, such as at least 15 Pa s, preferably at least 20 Pa s, more preferably at least 30 Pa s, most preferably at least 40 Pa s.

Phalloplasty

A further object of the invention is the use of a hydrogel comprising i) more than 6% polyacrylamide by weight, based on the total weight of the hydrogel, and ii) pyrogen-free water or saline solution for the preparation of an endoprosthesis for treating (reflux) oesophagitis. In a suitable embodiment, the hydrogel comprises more than 7, 8, or 9% polyacrylamide. This method for treating (reflux) oesophagitis comprising implanting or injecting a polyacrylamide hydrogel endoprosthesis wherein the hydrogel comprises more than 6% polyacrylamide by weight, based on the total weight of the hydrogel may be performed by implantation or injection of the endoprosthetic device, typically by injection or implantation of the device into the submucosal layer of the tissue.

The hydrogel typically further comprises at least 95% pyrogen-free water or saline solution. Thus, a particularly interesting embodiment comprises the use of a hydrogel comprising i) less than 1.6% polyacrylamide by weight, based on the total weight of the hydrogel and ii) at least 95% pyrogen-free water or saline solution for the preparation of an endoprosthesis for penis enlargement, preferably an injectable endoprosthesis. Injectable endoprostheses for penis enlargement typically have a complex viscosity of less than 20 Pa s, such as less than 18 Pa s, preferably less than 15 Pa s. Moreover said endprostheses typically have an elasticity module of less than 150 Pa, typically less than 100 Pa.

A still further object to the invention is the use of a hydrogel comprising i) more than 9.5% polyacrylamide by weight, based on the total weight of the hydrogel, and ii) pyrogen-free water or saline solution for the preparation of an implantable endoprosthesis for penis enlargement. This method of augmenting the size of a penis comprising the implantation of a polyacrylamide hydrogel endoprosthesis wherein the hydrogel comprises i) more than 9.5% polyacrylamide by weight, and ii) pyrogen-free water or saline solution may be performed by implantation or injection of the endoprosthetic device.

The hydrogel of the prosthetic device for penile augmentation comprising at least 9.5% polyacrylamide has a complex viscosity of at least 10 Pa s, such as at least 15 Pa s, preferably at least 20 Pa s, more preferably at least 30 Pa s, most preferably at least 40 Pa s. The high viscosity gels are suitable for implantation and have a semi-flacid to semi-rigid solid consistency, appropriate for this purpose.

Oesophagitis

A further object of the invention is the use of a hydrogel comprising i) more than 6% polyacrylamide by weight, based on the total weight of the hydrogel, and ii) pyrogen-free water or saline solution for the preparation of an endoprosthesis for treating (reflux) oesophagitis. In a suitable embodiment, the hydrogel comprises more than 7, 8, or 9% polyacrylamide. This method for treating (reflux) oesophagitis comprising implanting or injecting a polyacrylamide hydrogel endoprosthesis wherein the hydrogel comprises more than 6% polyacrylamide by weight, based on the total weight of the hydrogel may be performed by implantation or injection of the endoprosthetic device, typically be injection or implantation of into the submucosal layer of the tissue.

A still further object of the invention is the use of a hydrogel comprising i) less than 3.5% polyacrylamide by weight, based on the total weight of the hydrogel, and ii) pyrogen-free water or saline solution for the preparation of an endoprosthesis for treating (reflux) oesophagitis. This method for treating (reflux) oesophagitis may be by implanting or injecting an hydrogel wherein the hydrogel comprises less than 3.5% polyacrylamide by weight, based on the total weight of the hydrogel. In the treatment of (reflux) oesophagitis using a hydrogel comprising i) less than 3.5%, the hydrogel typically further comprises at least 95% water or saline solution and is typically performed by injection. In these embodiments, the degree of cross-linking may be such that the viscosity is at least 6.0 Pas, such as from 6.0 to 90 Pas, such as from 10 to 80 Pas, preferably from 20 to 80 Pas. The degree of cross-linking of the hydrogel used for the preparation of an endoprosthesis for treating reflux oesophagitis may be such that the elasticity module is from about 50 to 700 Pa such as 75 to 600, such as 100 to 500, preferably about 200 to 500 Pa. Typically, the hydrogel has a complex viscosity of at least 20 Pa s, more preferably at least 30 Pa s, most preferably at least 40 Pa s.

Body Contouring

A further object of the invention is the use of a hydrogel comprising i) more than 9.5% polyacrylamide by weight, based on the total weight of the hydrogel, and ii) pyrogen-free water or saline solution for the preparation of an implantable endoprosthesis for body contouring. This method of cosmetically altering a mammalian body (body contouring) comprising implanting a polyacrylamide hydrogel endoprosthesis, wherein the hydrogel comprises more than 9.5% polyacrylamide by weight, based on the total weight of the hydrogel, and ii) pyrogen-free water or saline solution may be performed by injection or implantation of the hydrogel into the soft-tissue of the patient.

The invention is further disclosed by the Examples which are not intended to be limiting in any way.

EXAMPLES

Example 1

Preparation of Hydrogel

The gel is a polyacrylamide gel manufactured by a polymerisation of the monomers of acrylamide and N,N'-methylene-bis-acrylamide. The finished product may have different viscosities.

Figure 1:
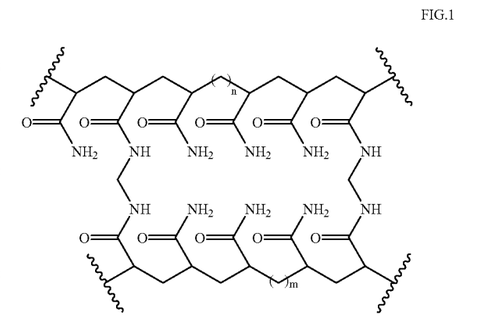

The hydrogel has the empirical formula $[C_3H_5NO]_x$ $[C_7H_{10}N_2O_2]_y$, and the structural formula as shown in FIG. 1

FIG.1

The hydrogel typically contains approximately 95% water. The concentration of the monomers acrylamide and N,N'-methylene-bis-acrylamide has been shown to be less than 10 ppm and is adequate for the desired stability of the final product, often less than 5 ppm.

The finished product must conform with respect to pH, absence of heavy metals, refractive index, stability, absence of pyrogens, and must be sterile, practically inert, and be substantially free of monomers.

Preparation 1.1

The synthetic preparation suitably involves the following operations:
1. Two mixtures, A1 and A2, are prepared. A1 comprises water, acrylamide, N,N'-methylene-bis-acrylamide, N,N,N',N'-tetramethylene-ethylene-diamine (TEMED). A2 comprises water and ammonium persulphate;
2. The two mixtures are combined in the following ratio: 1990 mL of A1 and 10 mL of A2 and kept at 45° C. and degassed with nitrogen for 20 seconds;
3. The reaction mixture is cast into several 100 mL beakers;
4. Polymerisation is allowed to occur for 0.5 to 1.5 hours;
5. The gel is demolded;
6. Residual monomers are extracted and with equilibration in WFI water for 92 hours, changing the water several times, typically 8 times during the 92 hours;
7. The purified gels are homogenised by grinding with an vertically oscillating grid;
8. The syringe is filled with the homogenised gel material;
9. Autoclavation of the syringe A typical method for preparing the hydrogel may be summarised as:

Preparation 1.2

Process Summary:

The gel is prepared by mixing an aqueous monomer solution of acrylamide (AM) and N,N'-methylene-bis-acrylamide (BISAM) as cross-linker with N,N,N',N'-tetramethylene ethylene diamine (TMED) as co-initiator and ammoniumpersulfate (APS) as free-radical initiator (redox-system). By degassing a bulk solution with nitrogen polymerisation starts. After final polymerisation the gel transferred into a washing tank with net trays onto which the gel is placed. During water washing the gel swells and monomer residues are extracted. The swollen gel is fed and evacuated in a filling unit having the gel delivered in a syringe, which is autoclaved.

Two alternate formulations have been prepared, a lower- and a higher-end viscosity formulation. Both formulations have a solid weight content of less than 3.5% and a complex viscosity in the range of 2 to 50 Pa s, typically between 3 and 20 Pa s.

TABLE 1

| Chemical constituent | lower end viscosity | higher end viscosity |
|---|---|---|
| acrylamide | 502 g | 547 g |
| N,N'-methylene-bis-acrylamide | 2,2 g | 4,6 g |
| TMED | 3,0 g | 2,6 g |
| APS | 5,4 g | 5,0 g |
| Non-pyrogenic water | Add 10 liter | Add 10 liter |

The above are typical preparations of the hydrogel and may be adjusted within certain ranges.

Preparation 1.3

Polyacrylamide Formulations from Inline Cross-linking Process

A particularly interesting method of preparing the hydrogels of the invention involves an inline cross-linking process. Two individual and eventually degassed flows, one being a pre-mix of acrylic amide, bis-methylene acryl amide (the cross-linker) and TEMED, the other being the AMPS initiator solution, are pumped into a static mixer for mixing, chemical initiation and subsequent extrusion downstream into a pipe reactor made of Teflon or steel in which the polymerisation occurs. Washing of the gel is simplified due to high surface area of gel from reactor.

By selecting monomer, cross-linker and initiator concentrations and their relative molar ratios, and by regulating the two flow rates and the polymerisation temperatures, it is possible to produce gels that are varying in degree of crosslinking and in solids content.

Preparation 1.4

The reagents were combined in ratios described in Tables 2, 3 and 4, and washed as described in the Tables (with pyrogen-free water unless indicated otherwise) to give low, medium, and high viscosity formulations. Hydrogels with solid weight contents between 0.5 and 25% polyacrylamide were prepared.

TABLE 2

Process parameters and features of resulting gel: low viscosity formulations

| | Iv1 | Iv2 | Iv3 | Iv4 | Iv5 | Iv6 | Iv7[d)] | Iv8[e)] | Iv9 | Iv10 | Iv11 | Iv11 | Iv12 |
|---|---|---|---|---|---|---|---|---|---|---|---|---|---|
| washing time (hrs) | [a)] | 19.5 | 73.75 | 92 | 94.3 | 72.8 | 93.6 | 93.9 | 121 | 96.4 | | | |
| dry matter[i)] (%) | 2.55 | 2.08 | 2.63 | 2.87 | 2.89 | 3.15 | 3.68 | 3.17 | 2.18 | (5.10)[f)] | (10.2)[f)] | (10.1)[f)] | (20.2)[f)] |
| | | 2.36 | 2.58 | 2.67 | 2.82 | 2.90 | 3.57 | 3.52 | | | | | |
| | | | 2.09 | | | | | | | | | | |
| molar ratio AM:bisAM | [b)] | 976 | 700 | 488 | 366 | 3239 | 488 | 488 | 701 | 701 | 488 | 488 | 488 |
| molar ratio AM + BISAM:TEMED | 252 | 252 | 253 | 251 | 252 | 249 | 252 | 252 | 252 | 252 | 252 | 504 | 2016 |
| molar ratio AM + BISAM:APS | 298 | 299 | 298 | 298 | 298 | 299 | 298 | 298 | 298 | 298 | 298 | 596 | 2385 |
| residual monomer in ppm | [c)] | 89 | 5 | 2.97 | 2 | 5 | 1,4 | 0.97 | 0.97 | | | | |
| elasticity G' in Pa | 0.16 | 5.23 | 14.3 | 26.6 | 57.05 | 71.7 | 39.2 | 28.5 | 28.5 | 11.1 | (911)[g)] | (1240)[g)] | (9460)[g)] |
| | | | 20.1 | | | | | | | | | | |
| viscosity in Pa s | .045 | .88 | 2.35 | 4.37 | 9.1 | 11.5 | 6.29 | 4.55 | 4.55 | 1.8 | (145)[g)] | (197)[g)] | (1505)[g)] |
| | | | 3.30 | | | | | | | | | | |

TABLE 2-continued

Process parameters and features of resulting gel: low viscosity formulations

| | Iv1 | Iv2 | Iv3 | Iv4 | Iv5 | Iv6 | Iv7[d] | Iv8[e] | Iv9 | Iv10 | Iv11 | Iv11 | Iv12 |
|---|---|---|---|---|---|---|---|---|---|---|---|---|---|
| gelation time (min) | liquid | highly viscous liquid | 12 | 2 | 2 | 2 | 2.5 | 2.5 | | 3.17 | 0.00 | 1.21 | 3.5[h] |

[a] material was liquid so washing was a dilution
[b] infinite
[c] since washing was not an extraction but a dilution, the residual monomer was merey decreased by the dilution factor (508 ppm to 254 ppm).
[d] casting and washing done using 0.9% NaCl aqueous solution
[e] casting with water; washing done using 0.9% NaCl aqueous solution
[f] pre-wash values-washing typically reduces value by 30–55%
[g] pre-eash values-washing typically reduces value by 20–40%
[h] highly notch sensitive
[i] variations in values may be due to measurement performance techniques or to location in the batch from which sample was taken

TABLE 3

Process parameters and features of resulting gel: medium viscosity formulations

| | mv1 | mv2 | mv3 | mv4 | mv5 |
|---|---|---|---|---|---|
| washing time (hrs) | 97 | 211.5 | 96 | 94.8 | 90.3 |
| dry matter (%) | 3.14 | 2.49 | 3.25 | 3.29 | 3.22 |
| molar ratio AM:bisAM | 310 | 310 | 290 | 289 | 289 |
| molar ratio AM + BISAM:TEMED | 252 | 252 | 252 | 251 | 252 |
| molar ratio AM + BISAM:APS | 299 | 299 | 299 | 299 | 299 |
| residual monomer in ppm | 1.6 | | 1.5 | | |
| elasticity G' in Pa | 108.5 | | 129 | 133.5 | |
| viscosity in Pa s | 17.4 | | 20.6 | 21.30 | |
| gelation time (min) | 2.5 | 2.5 | 2.18 | | |

TABLE 4

Process parameters and features of resulting gel: high viscosity formulations

| | hv1 | hv2 | hv3 | hv4 | hv5 |
|---|---|---|---|---|---|
| washing time (hrs) | 119.5 | 516 | 122 | 95.5 | 116.7 |
| dry matter (%) | 3.47 | 2.5 | 3.56 | 3.83 | 3.42 |
| molar ratio AM:bisAM | 260 | 260 | 260 | 260 | 260 |
| molar ratio AM + BISAM TEMED | 315 | 315 | 604 | 313 | 314 |
| molar ratio AM + BISAM:APS | 376 | 376 | 755 | 375 | 376 |
| residual monomer in ppm | 0.2 | | | | |
| elasticity G' in Pa | 343 | 274 | | 314.5 | |
| viscosity in Pa s | 54.7 | 43.65 | | 50.1 | |
| gelation time (min) | 2.18 | 2.18 | 7.5 | | |

Example 2
Analysis of Hydrogel
Characteristics of the Gel
The washed hydrogels will have typical properties outlined below.

TABLE 5

| Property | Low viscosity version | High viscosity version |
|---|---|---|
| Cross-linking density | 0,25% | 0,40% |
| Swelling rate | 80–120% | 50–70% |
| Rheol. elasticity modulus, G' | 10–80 Pa | 250–700 Pa |
| Rheol. Complex viscosity, $\eta^*$ | 2–10 Pas | 50–90 Pas |
| Dry matter | 1,6–3% | 3–5% |
| Refractive index | 1,335–1,338 | 1,338–1,340 |

Figure 2:
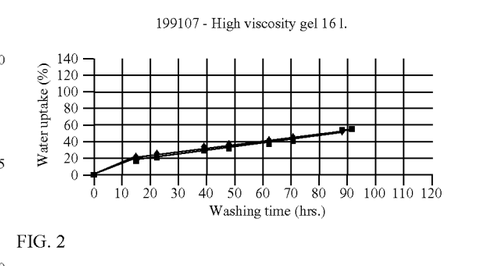
Figure 3:
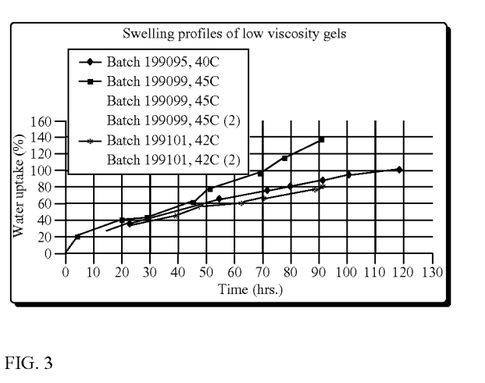

Example 3
Swelling occurs during wash procedure and will typically show a swelling profile as shown in FIGS. 2 and 3:

FIG. 2

FIG. 3

Example 4
Method of Administration for Reflux Oesophagitis

Treatment by Injection

The polyacrylamide hydrogel (solid weight content 2.5% and ca. 97.5% pyrogen-free water) is injected under the mucous membrane of the conduit between the oesophagus and stomach, such as to re-inforce the sphincter so as to provide increased density of the conduit. It is carried out during a short procedure involving few complications.

Example 5
Method of Administration for Body Contouring

Treatment by Injection
a) The injection of the gel may be performed under local anaesthesia.
b) The procedure must be performed under sterile conditions. Pharmaceuticals are not to be injected into the gel
c) The gel is pre-filled in sterile syringes of 1 mL with luer-lock and should be injected subcutaneously with a thin gauge needle, e.g. 27 G. Needles should be CE-marked.
d) Inject the necessary amount of the gel subcutaneously in a retrograde manner by injecting the gel while withdrawing the needle. A patient record label is part of the packaging and is removable and to be attached to the patient record to ensure that the product is traceable.
e) After the injection is performed, a light manipulation may be performed in order to obtain an even or desired distribution of the gel. The injected gel will form a stable, soft part in the connective tissue and will give long lasting cosmetically satisfactory appearance.
f) Further injection sessions may be performed to achieve the desired affect.

Treatment by Implantation

The gel, optionally in sealed in a silicone-based envelope is placed subcutaneously into the soft tissue of the patient.

The invention claimed is:

1. A bio-stable hydrogel for use as an endoprosthesis in a mammal, said hydrogel, prior to being administered as an endoprosthesis, consisting essentially of:
   a cross-linked polyacrylamide which includes a cross-linked polymer of acrylamide and methylene bis-acrylamide, wherein the acrylamide and methylene bis-acrylamide are combined in a molar ratio of 150:1 to 1000:1 and wherein the hydrogel comprises about 0.5 to less than 3.5% of the polyacrylamide by weight, based on the total weight of the hydrogel, and
   water or an aqueous solution,
   wherein the hydrogel comprises less than 50 ppm of acrylamide and methylene bis-acrylamide monomers; and wherein the hydrogel has an elasticity module from about 10 to 700 Pa and a complex viscosity from about 2 to 60 Pas,
   wherein the hydrogel is resistant to biological degradation, and
   wherein the hydrogel is not water-soluble.

2. A bio-stable hydrogel for use as an endoprosthesis in a mammal, said hydrogel, prior to being administered as an endoprosthesis, comprising:
   a cross-linked polyacrylamide which consists essentially of a cross-linked polymer of acrylamide and methylene bis-acrylamide, wherein the acrylamide and methylene bis-acrylamide are combined in a molar ratio of 150:1 to 1000:1 and wherein the hydrogel comprises about 0.5 to less than 3.5% of the polyacrylamide by weight, based on the total weight of the hydrogel, and
   water or an aqueous solution,
   wherein the hydrogel comprises less than 50 ppm of acrylamide and methylene bis-acrylamide monomers; and wherein the hydrogel has an elasticity module from about 10 to 700 Pa and a complex viscosity from about 2 to 60 Pas,
   wherein the hydrogel is resistant to biological degradation, and
   wherein the hydrogel is not water-soluble.

3. A bio-stable hydrogel for use as an endoprosthesis in a mammal, said hydrogel, prior to being administered as an endoprosthesis, comprising:
   about 0.5% to less than 3.5%, based on the total weight of the hydrogel, of a polymer consisting essentially of a cross-linked polyacrylamide and methylene bis-acrylamide, wherein the acrylamide and methylene bis-acrylamide are combined in a molar ratio of 150:1 to 1000:1, and
   at least 95% water or an aqueous solution,
   wherein the hydrogel comprises less than 50 ppm of acrylamide and methylene bis-acrylamide monomers; and wherein the hydrogel has an elasticity module from about 10 to 700 Pa and a complex viscosity from about 2 to 60 Pas,
   wherein the hydrogel is resistant to biological degradation, and
   wherein the hydrogel is not water-soluble.

4. A hydrogel according to claim 1 or 2 wherein the hydrogel comprises at least 95% by weight water or aqueous solution based on the total weight of the hydrogel.

5. A hydrogel according to claim 1, comprising at least 1% by weight of the polyacrylamide, based on the total weight of the hydrogel.

6. A hydrogel according to claim 1, which has a complex viscosity from about 5 to 60 Pas.

7. A hydrogel according to claim 1, which has an elasticity module of not less than 20 Pa.

8. A hydrogel according to claim 1, which has an elasticity module from about 35 to 480 Pa.

9. A hydrogel according to claim 1, which has a cross-linking density of about 0.2 to 0.5%.

10. A hydrogel according to claim 1, wherein the acrylamide and methylene bis-acrylamide are combined in the molar ratio of from 175:1 to 800:1.

11. A hydrogel according to claim 1, for use as an implantable endoprosthesis.

12. A hydrogel according to claim 1, for use as an injectable endoprosthesis.

13. A hydrogel according to claim 1, wherein the complex viscosity is from 6 to 40 Pas.

14. A hydrogel according to claim 1, for use in an implantable endoprosthesis comprising a silicone-based envelope.

15. A hydrogel according to claim 1 further comprising cells for cellular engraftment.

16. A hydrogel according to claim 1 which comprises 0.5 to 3.47% of the polyacrylamide by weight, based on the total weight of the hydrogel.

17. A hydrogel according to claim 1 which comprises 0.5 to 3.4% of the polyacrylamide by weight, based on the total weight of the hydrogel.

18. A hydrogel according to claim 1 which comprises 0.5 to 3.3% of the polyacrylamide by weight, based on the total weight of the hydrogel.

19. A hydrogel of claim 1, 2 or 3, wherein the hydrogel is substantially free of any other polymeric content.

* * * * *